United States Patent
Yacoubian

(10) Patent No.: US 7,610,106 B2
(45) Date of Patent: Oct. 27, 2009

(54) EPICARDIAL HEARTWIRE WITH CHEST TUBE

(76) Inventor: Vahe S. Yacoubian, 610 N. Central Ave., Suite 105, Glendale, CA (US) 91203

( * ) Notice: Subject to any disclaimer, the term of this patent is extended or adjusted under 35 U.S.C. 154(b) by 444 days.

(21) Appl. No.: 10/534,309

(22) PCT Filed: Nov. 6, 2003

(86) PCT No.: PCT/US03/35875

§ 371 (c)(1),
(2), (4) Date: Oct. 11, 2005

(87) PCT Pub. No.: WO2004/043518

PCT Pub. Date: May 27, 2004

(65) Prior Publication Data

US 2006/0100683 A1     May 11, 2006

Related U.S. Application Data

(60) Provisional application No. 60/424,537, filed on Nov. 7, 2002.

(51) Int. Cl.
*A61N 1/05* (2006.01)
(52) U.S. Cl. .................. 607/130; 607/119; 607/129
(58) Field of Classification Search .................. 607/116, 607/119, 129, 130, 152
See application file for complete search history.

(56) References Cited

U.S. PATENT DOCUMENTS 3,902,501 A    9/1975    Citron et al. ................. 128/418

(Continued)

FOREIGN PATENT DOCUMENTS

JP    3-112566    5/1991

(Continued)

OTHER PUBLICATIONS

International Search Report for PCT/US03/35875 dated May 4, 2004.

*Primary Examiner*—Kennedy J Schaetzle
(74) *Attorney, Agent, or Firm*—Inskeep IP Group, Inc.

(57) ABSTRACT

A heartwire comprises a wire having a proximal end and a distal end, at least part of the distal end being conductive so as to be usable in heart stimulation; and attached to said distal end, an end structure adapted for non-invasively maintaining the distal end in position adjacent the heart. The end structure may comprise an irregular or three-dimensional, atraumatic structure adapted for engaging a surgical material secured to the heart, for maintaining said heartwire in position relative to said surgical material. The surgical material may be a pledget, and the end structure may comprise at least one of a pigtail, a hook, a tine and a suture sized and shaped for engaging the pledget so as to maintain the heartwire in position. The heartwire may comprise a second wire having a corresponding distal end structure and may be a bipolar heartwire. An arrangement for stimulating a heart may comprise the foregoing heartwire, in combination with a surgical material for being secured to the heart. The heartwire may be combined with and/or secured to a chest tube, and may be removable from the chest tube while still in position relative to the heart. A chest tube may also be combined with an anesthesia delivery tube and/or a wire for carrying cardiac output monitoring signals.

11 Claims, 7 Drawing Sheets

U.S. PATENT DOCUMENTS

| | | | |
|---|---|---|---|
| 3,939,843 A | 2/1976 | Smyth | 128/404 |
| 4,166,469 A | 9/1979 | Littleford | 128/784 |
| 4,338,947 A | 7/1982 | Williams | |
| 4,809,713 A | 3/1989 | Grayzel | 128/785 |
| 4,883,070 A | 11/1989 | Hanson | 128/785 |
| 4,938,231 A | 7/1990 | Milijasevic et al. | 128/784 |
| 4,962,767 A | 10/1990 | Brownlee | 128/786 |
| 5,090,422 A | 2/1992 | Dahl et al. | 128/784 |
| 5,127,421 A | 7/1992 | Bush et al. | 128/785 |
| 5,255,692 A | 10/1993 | Neubauer et al. | 607/122 |
| 5,261,419 A | 11/1993 | Osypka | 607/122 |
| 5,314,463 A | 5/1994 | Camps et al. | 607/129 |
| 5,356,427 A | 10/1994 | Miyata et al. | 607/122 |
| 5,383,924 A | 1/1995 | Brehier | 607/126 |
| 5,489,294 A | 2/1996 | McVenes et al. | |
| 5,527,358 A * | 6/1996 | Mehmanesh et al. | 607/129 |
| 5,549,615 A | 8/1996 | Hocherl et al. | 606/108 |
| 5,647,857 A | 7/1997 | Anderson et al. | 604/264 |
| 5,649,975 A | 7/1997 | Lindegren et al. | 607/126 |
| 5,735,891 A | 4/1998 | White | 607/126 |
| 5,772,693 A | 6/1998 | Brownlee | 607/123 |
| 5,775,328 A | 7/1998 | Lowe et al. | 128/662.06 |
| 5,983,142 A | 11/1999 | Bridges | 607/119 |
| 6,216,042 B1 | 4/2001 | Robertson | 607/115 |
| 6,231,514 B1 | 5/2001 | Lowe et al. | 600/462 |
| 6,256,543 B1 | 7/2001 | Spence | 607/130 |
| 6,330,481 B1 | 12/2001 | Van Wijk et al. | 607/129 |
| 6,334,873 B1 | 1/2002 | Lane et al. | 623/2.14 |
| 6,532,387 B1 | 3/2003 | Marchitto et al. | 604/21 |
| 6,562,049 B1 | 5/2003 | Norlander et al. | 606/108 |

FOREIGN PATENT DOCUMENTS

| | | |
|---|---|---|
| JP | 7-222807 | 8/1995 |
| JP | 2001-87397 | 4/2001 |
| WO | WO 93/09840 | 5/1993 |

* cited by examiner

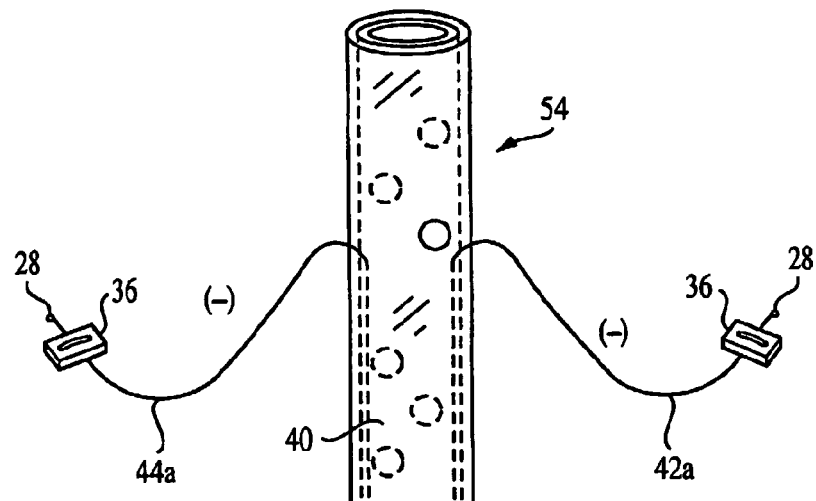
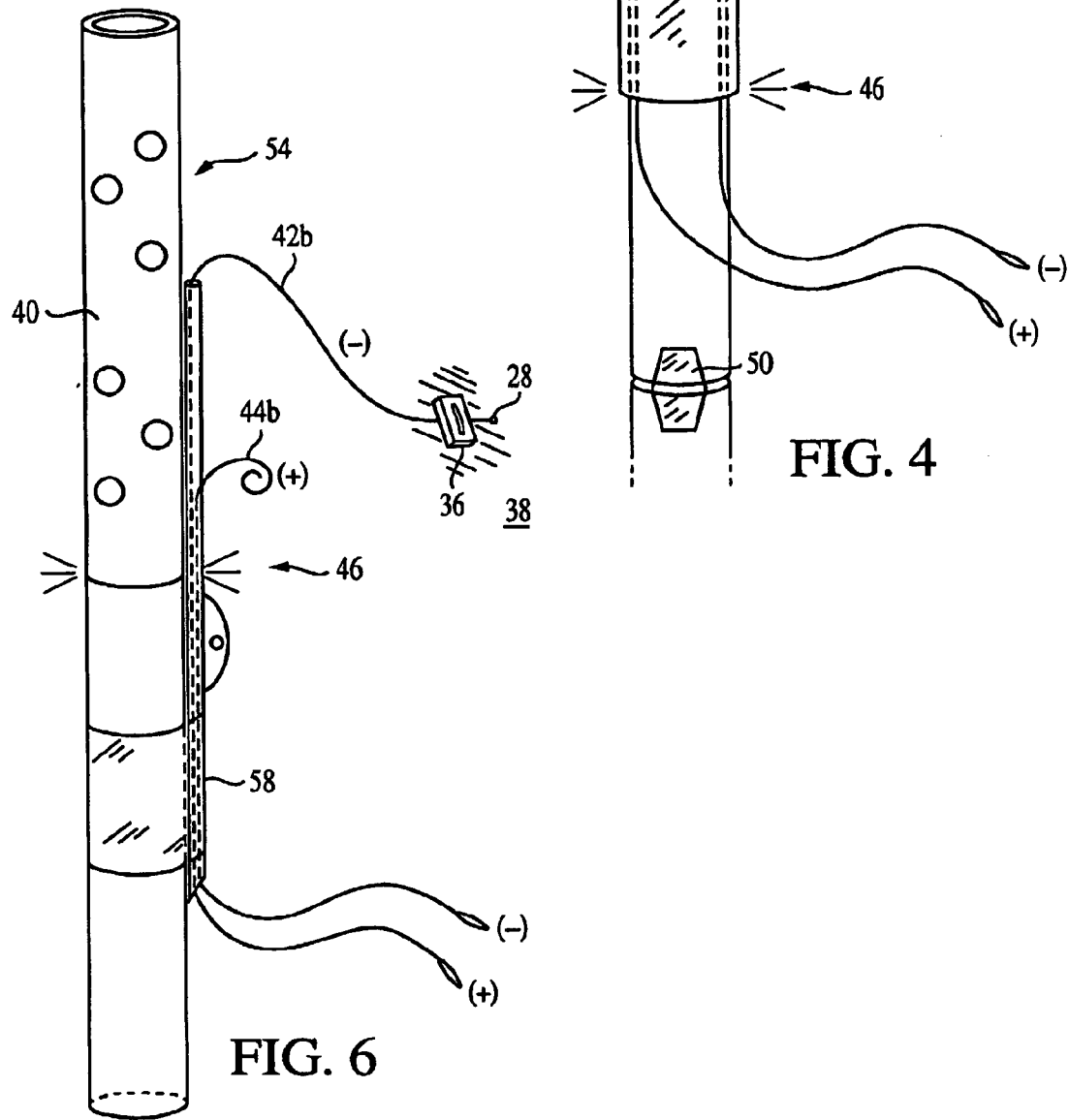
FIG. 4
FIG. 6

EPICARDIAL HEARTWIRE WITH CHEST TUBE

CROSS REFERENCE TO RELATED APPLICATION

The present application is a 35 U.S.C. 371 national phase conversion of PCT/US2003/035875 filed 6 Nov. 2003, which claims priority of U.S. Provisional Application No. 60/424,537 filed Nov. 7, 2002.

BACKGROUND OF THE INVENTION

1. Field of the Invention

The present invention relates to an epicardial heartwire (also called a temporary myocardial pacing wire or stimulation lead), a combination of a chest tube and an epicardial heartwire, and a method of using the same.

2. Related Art

Conventionally, heartwires are positioned epicardially to the myocardium and stitched or passed through a myocardial tunnel. Typically, they stay between one and seven days in the myocardium, usually for 1-2 days, and preferably less than 7 days, after open-heart surgery. Before the patient is released from the hospital, the heartwires are pulled out of the myocardium.

A problem that occurs sometimes is that, during the pullout process, the myocardial tissue is injured or disturbed and starts bleeding again. Also, since epicardial heartwires are normally placed underneath the skin in the form of a loop, the loop of a wire being pulled out may catch a vein or other structure, which can be fatal for the patient. This risk is especially dangerous when a loop of wire becomes tangled around a vein graft, which may moreover have metallic clips applied at its branching sites.

There is a need for an improved arrangement which can avoid the foregoing problems.

SUMMARY OF THE INVENTION

According to one aspect of the invention, there is provided a unipolar or bipolar heartwire, which can be placed on the myocardium without having to be passed through the myocardium, and a method of using the same.

After every open-heart surgery, small pledgets made of a biocompatible cotton or Teflon material are stitched to the heart by very fine Prolene sutures to repair or close the heart. Other biocompatible materials may of course be used. These pledgets are permanently sutured to the myocardium. According to this aspect of the invention, a heartwire is placed underneath a pledget, between the pledget and the myocardium, for temporary pacing. An irregular or three-dimensional structure such as a silastic coil or pigtail, or another atraumatic anchor mechanism such as silastic tines or a crimped Prolene suture, at the distal end of the heartwire, keeps the heartwire in place underneath the pledget. Other materials may of course be used. For removal, such a structure can easily be pulled out from underneath the pledget without injuring the myocardium.

The invention is advantageous in that it uses the standard pledget and sutures to fix the heartwire, not requiring additional sutures for this purpose, so that there is less chance of injuring the myocardium when the heartwire is pulled out after several days. Further, the cost of materials is reduced.

According to a second aspect of the invention, a chest tube is combined with a heartwire. Chest tubes are used to evacuate blood from the mediastinum (interpleural space) after open-heart surgery. They are also used to evacuate blood and air from the thoracic cavity after thoracotomy for lung or pleural surgery. The chest tube stays in the mediastinum after heart surgery for one to three days depending on the amount of post-operative drainage present.

One or two chest tubes are used to drain blood after every open-heart surgery, and to monitor the bleeding thereafter. Chest tubes are typically located very close to the heart and extend out of the patient's chest through the skin and they are fixed with a suture in that location. The suture is tied to close the chest tube exit site. In the majority of cases, chest tubes are removed within 2-3 days after surgery. Temporary pacing wires are also removed after 2-3 days in the majority of cases. A commonly-used type of chest tube is a plastic tube made of biocompatible rubber, which is between 20 and 40 cm long, and has holes at the distal section. The holes allow the excess blood to enter the chest tube. The chest tube itself is connected to a vacuum machine.

The chest tube of this aspect of the invention has an elongated structure, such as one or two grooves formed in its side, where a unipolar or bipolar heartwire is embedded. The heartwire is held in place in the chest tube by a peelable film. By inserting the chest tube, a heartwire is inserted at the same time. After insertion of the chest tube, the heartwire can be peeled from the chest tube, depending how much length is needed for the heartwire to reach the myocardium. The heartwire is preferably but not necessarily similar to the one described above in connection with the first aspect of the invention.

According to another aspect of the invention, a fixation wing is attached to the chest tube and the pacing wire or wires run lengthwise through the fixation wing. Manufacture is simplified by this form of the invention, since it does not require formation of grooves in the chest tube.

An advantage of these combinations is that when it is time for the chest tube and the heartwire to be removed, they can be pulled out together. Another advantage is that the pacing wires follow a direct path to the heart, so that there are no loops. Thus, there is reduced chance of a heartwire being tangled on a metallic clip or anything else at the site of vein graft branches.

In this connection, it is unnecessary for the heartwire to be secured to or embedded in the chest tube near the distal end of the chest tube. Leaving the heartwire unattached to the distal end of the chest tube simplifies manufacture, since the drainage holes can be formed without any consideration of the heartwire; the groove or other securement for the heartwire can be made shorter; and the heartwire can more readily be pulled away from the chest tube for use.

Another advantage of the invention is that the chest tube can incorporate the ground pole to the temporary heartwire.

Further, since the wires are separable from the chest tube it becomes possible to remove the chest tube first, leaving the heartwire(s) in place for continued use. In 90% of cases, both chest tubes and pacing wires are used and can be removed together, at the same time. In some patients, however, the pacing wires might need to stay for few more days after chest tube removal.

Additional advantages of the invention are as follows: It eliminates any necessity to leave loops of wire on or near the surface of the heart, by combining the chest tube and the heartwire together so as to permit shortening the heartwire length. It does not require the pacing wire to be in a myocardial tunnel, but rather lets the wire sit on the epicardium (the outer covering of the heart) and prevents its dislodgment by suturing a Teflon or other material pledget on the myocardium over the pacing wire and tie. It may permit all cardiac surgery patients to have pacing wires for at least 1-2 days, so that they can be paced immediately if the need arises. Once the chest tube is removed, the pacing wires come out together with the chest tube. There is less risk of bleeding from the site of pacing wire fixation, as there is no myocardial tunnel which could be a source of bleeding. It may remove the need to monitor patients' blood pressure and pulse for 2 hours after pacing wire removal, a protocol many heart centers follow at present. Further, the chest tube can be removed with the pacing wires still in place, if pacing is still needed.

Even conventional pacing wires can be made safer with the disclosed technique of epicardial fixation of temporary pacing wires with, for example, a Teflon pledget and a silastic coil at the end of the pacing wire.

According to yet another aspect of the invention, a chest tube may be combined with at least one tube, preferably at least two tubes, for delivering post-operative local anesthesia to the chest cavity, particularly to the intercostal nerves which run on either side of the sternum inferior to the ribs. (See FIG. 11.) This anesthetic delivery system can reduce post-operative surgical pain, possibly obviating the use of opiates, with their well-known disadvantages. Pacing heartwires can be combined with the chest tube as described elsewhere herein, in addition to the anesthetic delivery tubes.

Other features and advantages of the present invention will become apparent from the following detailed description of embodiments of the invention, which refers to the accompanying drawings, in which like references denote like elements and parts and redundant explanations are omitted.

BRIEF DESCRIPTION OF THE DRAWINGS

FIG. 4 shows a variation on the embodiment of FIGS. 2 and 3.

FIGS. 5 and 6 show a combined heartwire and chest tube according to a third embodiment of the invention.

DETAILED DESCRIPTION OF EMBODIMENTS OF THE INVENTION

Figure 1A:
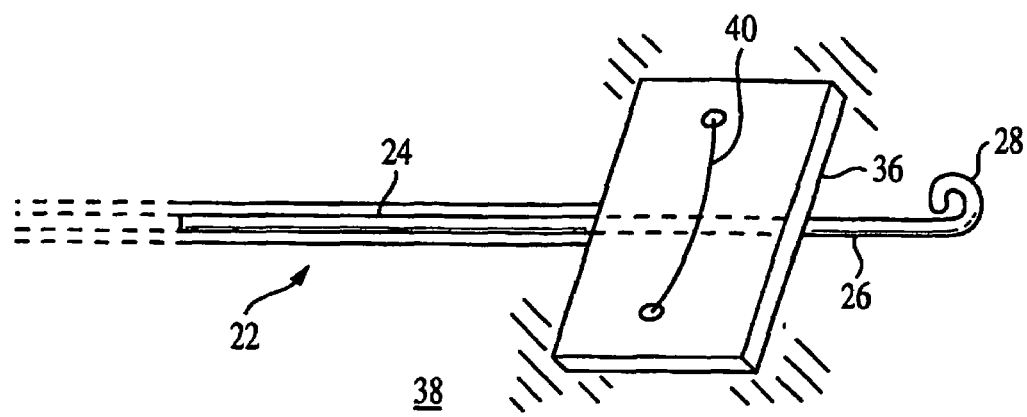
FIGS. 1A and 1B show an epicardial heartwire according to a first embodiment of the invention.
Figure 1B:
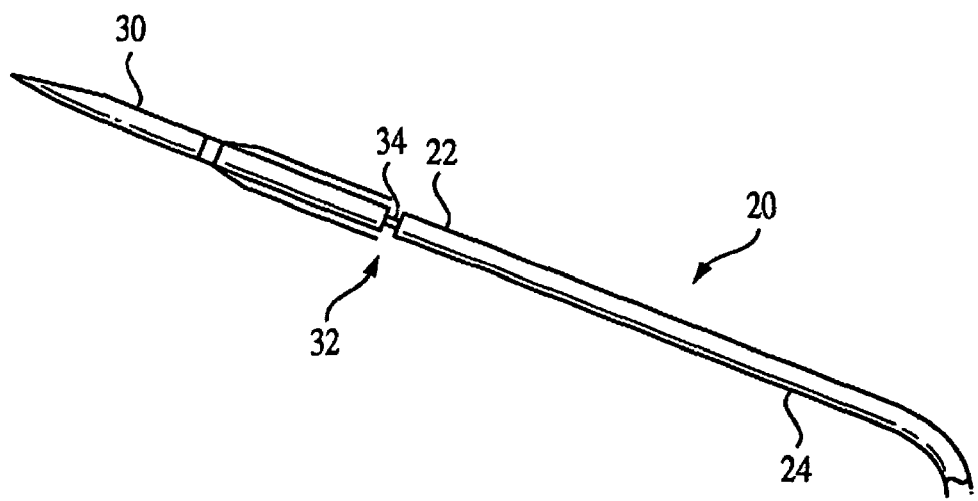
Figure 1B:
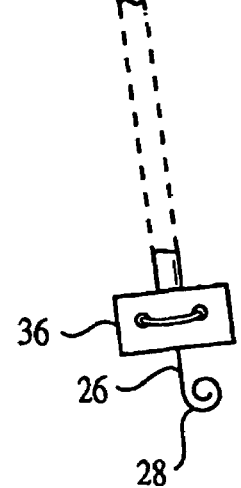

FIGS. 1A and 1B show an epicardial heartwire 20 according to a first embodiment of the invention, having a proximal end 22 and a distal end 26. Biocompatible insulation 24 covers most of the wire. At the opposite end of the heartwire is a distal end or pole 26 where the wire is bare. An insulated pigtail 28 which comprises for example a coiled silastic or silicone or other insulating material is attached to the distal pole by any convenient means. Another atraumatic structure such as tines, hooks or a coil may be substituted for the pigtail 28.

FIGS. 1A and 1B also show a conventional pledget 36. The pledget is shown connected to the myocardium of a patient 38 in conventional fashion, for example by a Prolene suture 40.

The distal pole 26 of the heartwire 20 is placed underneath the pledget 36, between the pledget and the myocardium, for providing electrical contact for pacing. The pigtail 28 extends under and past the pledget and holds it in place there.

The heartwire 20 may be attached to a chest tube as described hereinbelow, or may be used alone. As seen in FIG. 1B, the proximal end 22 of the heartwire 20 may exit the mediastinum and through the skin by means of a sharp chest needle 30; whereupon the needle is broken off at a break point 32, exposing connector pins 34 to be connected to a pacemaker.

Figures 2, 3:
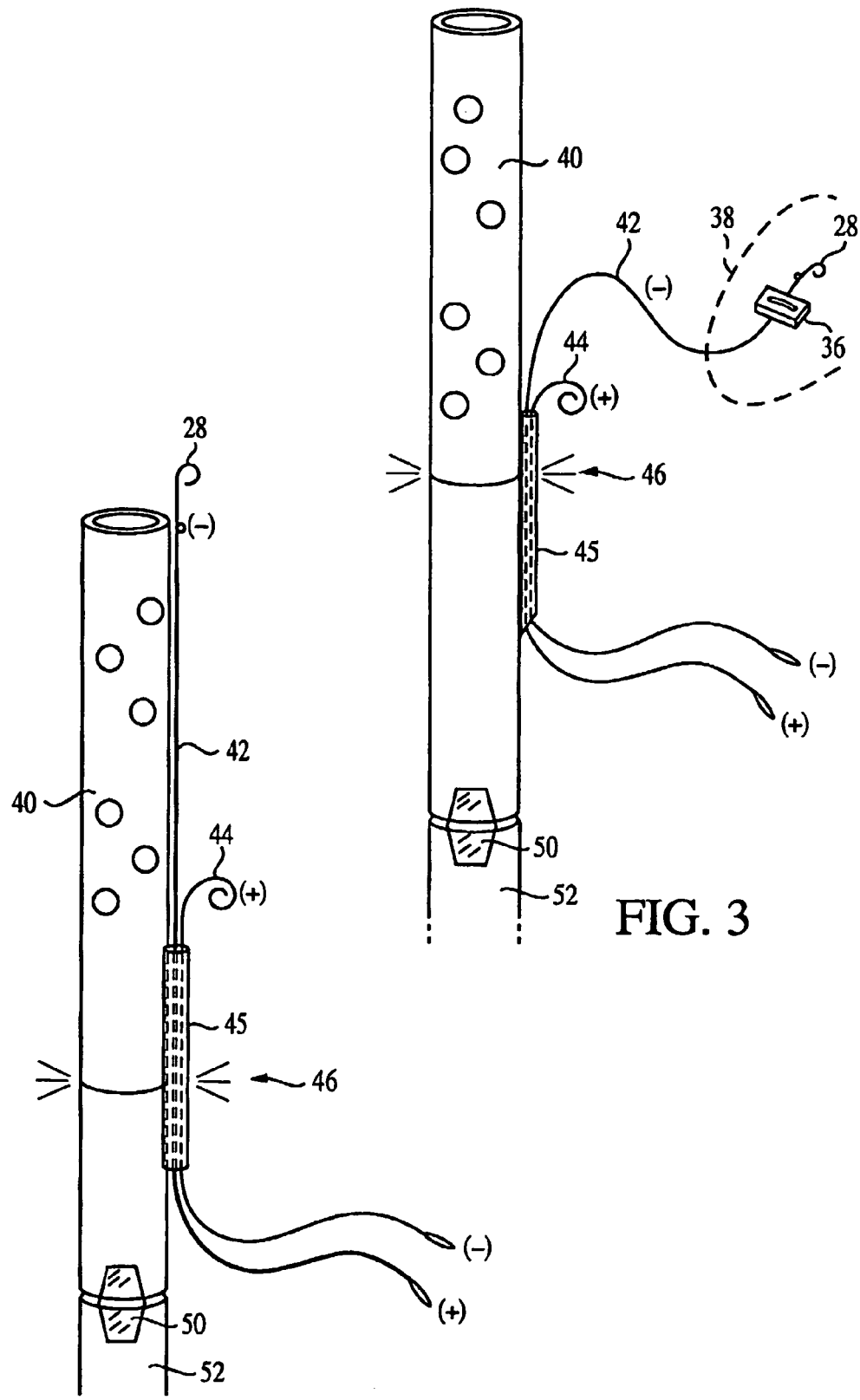
FIGS. 2 and 3 show a combined heartwire and chest tube according to a second embodiment of the invention.

A first example of a combined heartwire and chest tube 40 is shown in FIGS. 2 and 3. In this example, there are two heartwires. One heartwire 42 extends to the distal end of the chest tube and the second heartwire 44 extends into the chest just past the skin level 46. The second heartwire 44 is used for grounding. In use, it will be in contact with the subcutaneous tissues and beyond, without necessarily being fixed to such tissues with stitches.

The first heartwire 42 is secured to an elongated structure on the chest tube. In this embodiment, the elongated structure is a groove or channel (not shown) formed in an outside portion of the chest tube 40 and covered there by a silastic or other thin film (not shown). Also shown is an optional conduit 45 for the heartwires 42 and 44 which may be included if desired but is not necessary in this embodiment.

As shown in FIG. 3, during surgery the film easily releases. The first heartwire 42 is pulled away from the chest tube and is moved to a selected position on the myocardium 38 and attached there via a pledget 36 as described above.

In use, the first heartwire 42 is usually the negative pole and is placed on the atrium for atrial pacing. The second heartwire 44 is the positive lead and is connected to ground. For ventricular pacing the first heartwire 42 is placed on the ventricle and is connected to the negative pole of the pacemaker. The positive pole of the pacemaker is connected to the ground pacing wire which is in contact with the subcutaneous tissues. Only the first heartwire 42, that is the negative lead, needs to enter the chest cavity. In appropriate cases, no separate ground lead is even needed, if a ground pole is provided on the chest tube so as to make good electrical contact with the patient's tissues 2-3 cm from the point of exit from the mediastinum through the skin.

Thus, the second heartwire 44 on the chest tube 40 need not extend further than the skin level 46 near the proximal end of the chest tube. There can be a simple ground pole or terminal on the exterior of the chest tube, or a short lead may be connected to that portion of the second heartwire as well. It need not even be placed in a channel or groove in the wall of the chest tube, since it does not need to extend a significant distance into the chest cavity.

Also seen in FIGS. 2-3 is a connector 50 which connects the chest tube 40 to a suction tube 52.

Referring now to FIG. 4, a variation of the previous embodiment is seen. By connecting a ground lead to the ventricle and the negative lead to the atrium, atrio-ventricular (AV) sequential pacing becomes possible. The negative lead 44a is attached to the atrium, and the positive (grounded) lead 42a is connected to the ventricle, again, via respective pledgets. AV pacing provides increased cardiac output over either atrial or ventricular pacing. It mimics the normal contraction of the heart. AV pacing can also be accomplished by an embodiment of the invention (not shown) wherein two chest tube/heartwire combinations similar to that in FIGS. 2-3 are used respectively for pacing an atrium and a ventricle. In such an arrangement the short ground wires on the respective chest tubes are not used.

Figure 11:
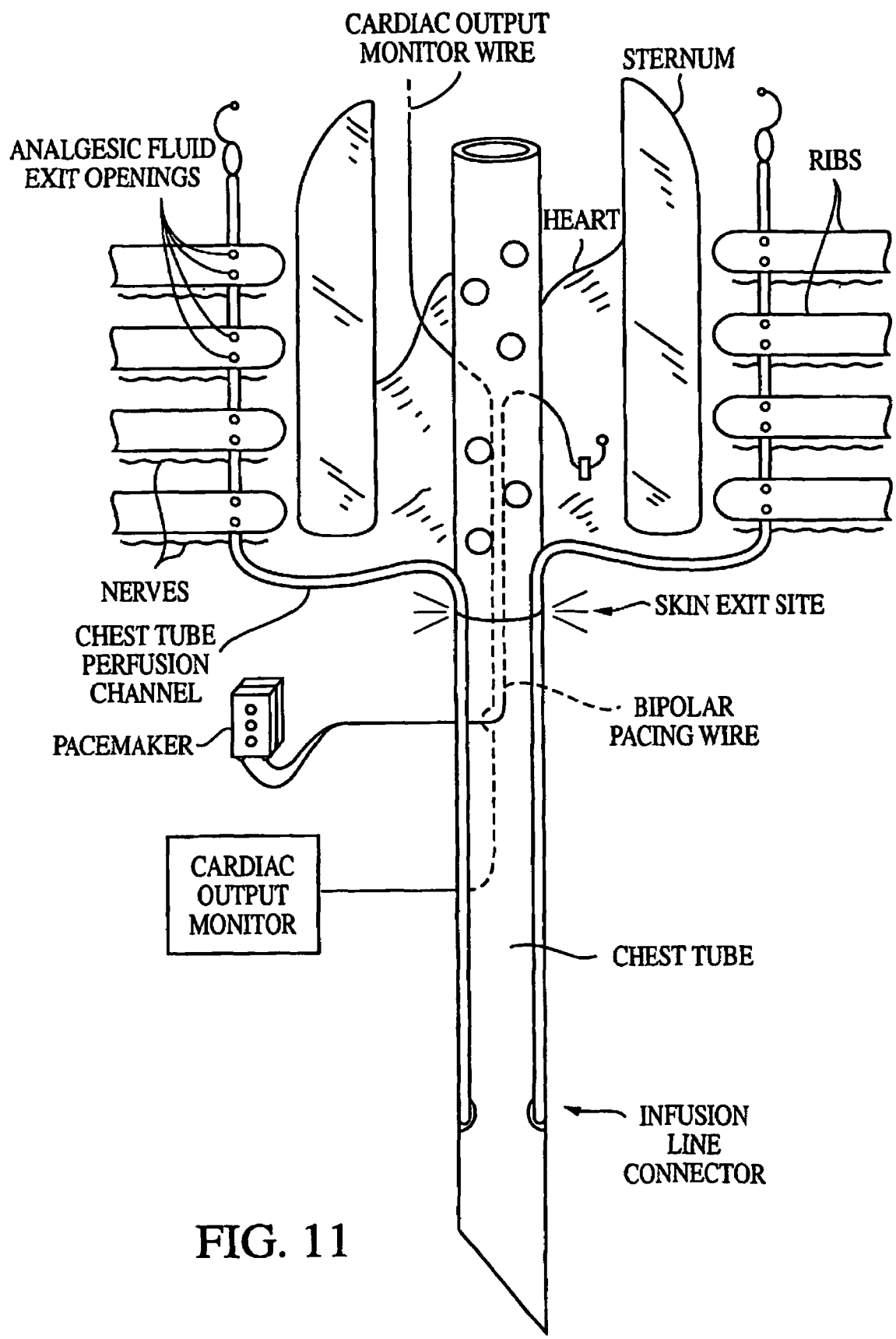
FIG. 11 shows another embodiment of the invention, which may include an anesthetic delivery tube and/or a cardiac output monitor wire.

Obviously even atrio-biventricular pacing is possible if two ventricular and one atrial lead are used (embodiments of chest tubes containing three leads or 2 chest tubes might be required for such pacing). A chest tube can also contain a wire to be connected to the great vessels or cardiac chambers with a stitch. The wire can be connected to a device for measuring cardiac output, for example by measuring electrical impedance, or to another physical means for measuring cardiac output, during surgery and/or postoperatively. (See FIG. 11.) This cardiac output monitor wire, and the anesthetic delivery tube(s) and pacing wire(s) described elsewhere, can be included with a chest tube either individually or in any combination.

In FIG. 4, it is again seen that neither of the heartwires 42a, 44a needs to or does extend to the distal end 54 of the chest tube 40. The heartwires may be disposed in grooves (not shown) and covered by films (not shown) as in the embodiment of FIGS. 2-3. They may alternatively be adhered to the chest tube 40 by another suitable elongated structure or other means. Again, they are secured to the myocardium 38 via respective pledgets 36 and pigtails 28.

Figure 5:
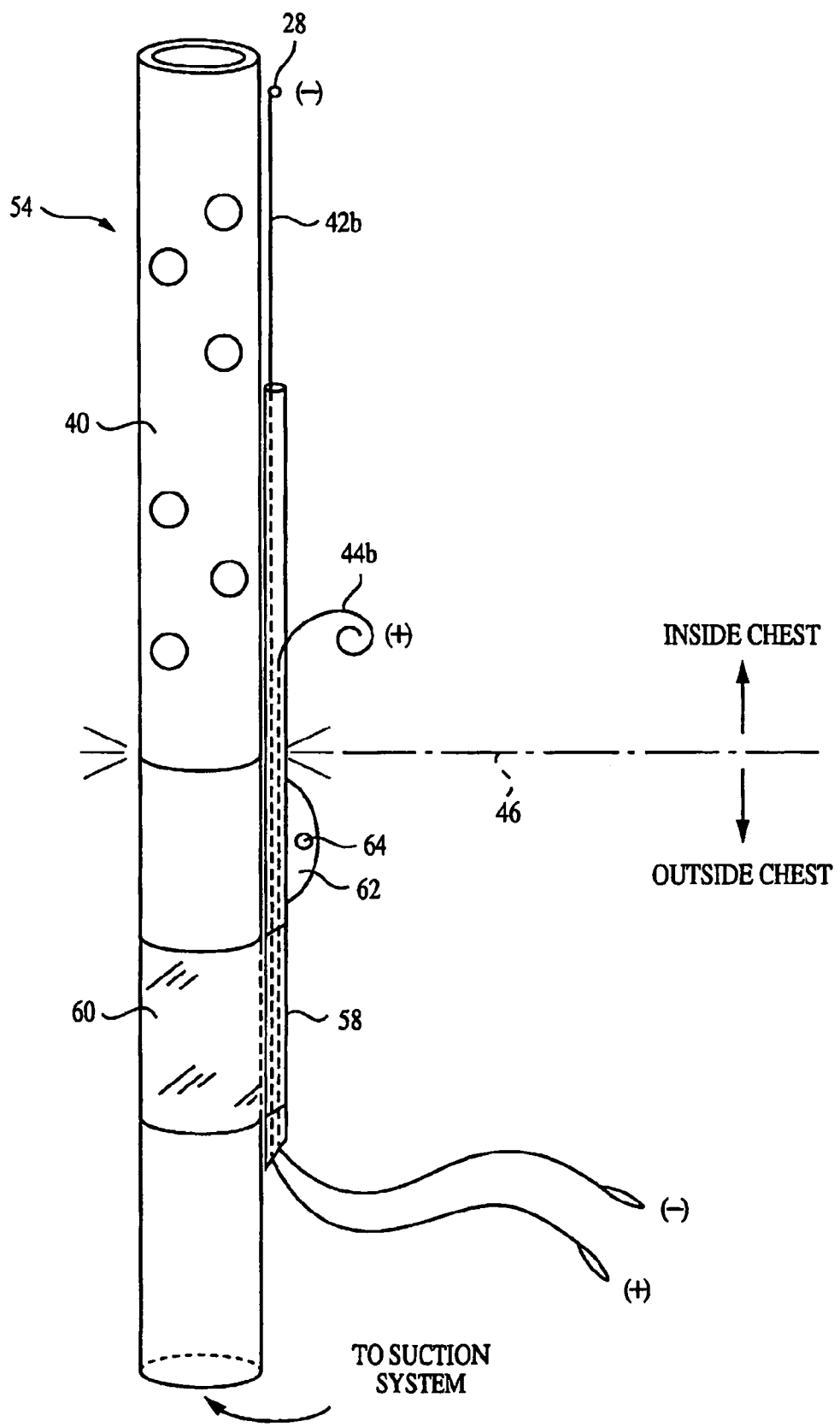

FIGS. 5 and 6 show a third embodiment of the invention. A chest tube 40 has a first wire 42b and a second wire 44b fixed to the chest tube 40 by a pacing system fixation wing 58. The wing 58 is in turn fixed to the chest tube by a thin plastic film 60 or another suitable means, which is easily removable if it is desired to remove the chest tube without removing the heartwires.

As seen in FIG. 5, the first wire 42b need not be fixed to the distal end 54 as described above. It is shown free of the distal end 54 in FIG. 6. If it is initially fixed to the distal end 54, then it is separated at the time of use and placed in the position shown in FIG. 6.

In the embodiment of FIGS. 5-6, the wires 42a, 44b pass through a longitudinal lumen formed in the fixation wing 58. However, they may be adhered to the fixation wing 58 in any other suitable way as well.

This embodiment may for example be used for ventricular pacing by connecting the short ground (+) wire 44b to the ground (+) pole of the pacemaker. The longer (−) wire 42b is connected to the heart ventricle 38 and to the (−) pole of the pacemaker.

Figures 7, 8:
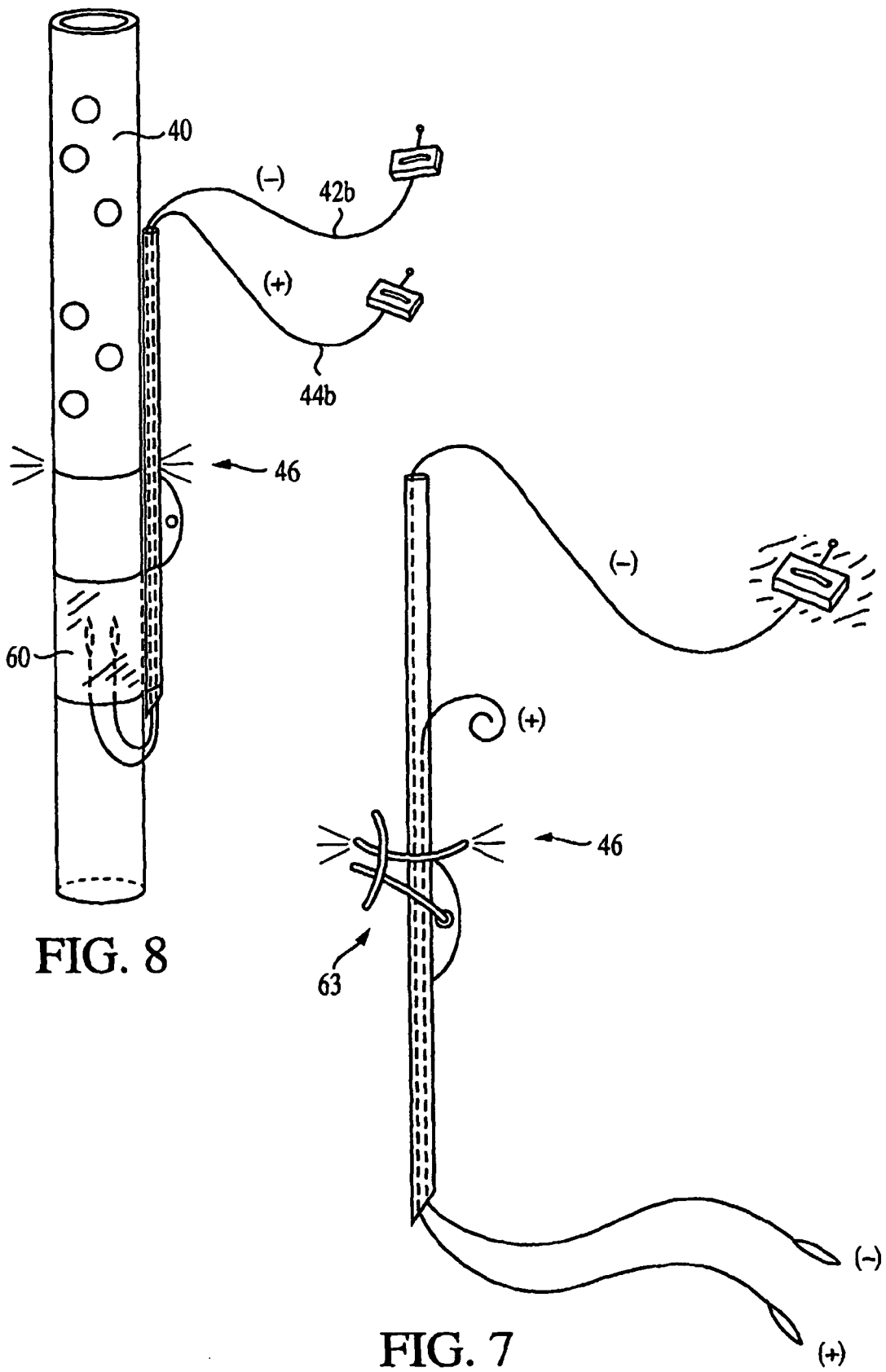
FIG. 7 shows the embodiment of FIGS. 5 and 6, after removal of the chest tube.
FIG. 8 shows a modification of the embodiment of FIGS. 5 and 6.

FIG. 7 shows the preceding embodiment of the invention after removal of the chest tube 40. The fixation wing 58 is sutured to the patient at the skin level 46, by a suture 63 passing through the hole 64 formed in the extension tab 62 of the fixation wing 58. The suture 63 is the same suture that was used at the time of surgery to close the chest tube exit site. Once the chest tube is removed and the suture is cut, the same suture is then tied, closing the wound and, prior to cutting, one limb of the suture is passed through the hole in the fixation wing and tied with the other limb, fixing the pacing wires to the skin.

FIG. 8 shows a modification of FIGS. 5-6, in which the proximal ends of the wires 42b and 44b are shown secured to the chest tube 40 by the plastic film 60 prior to use.

Figure 9:
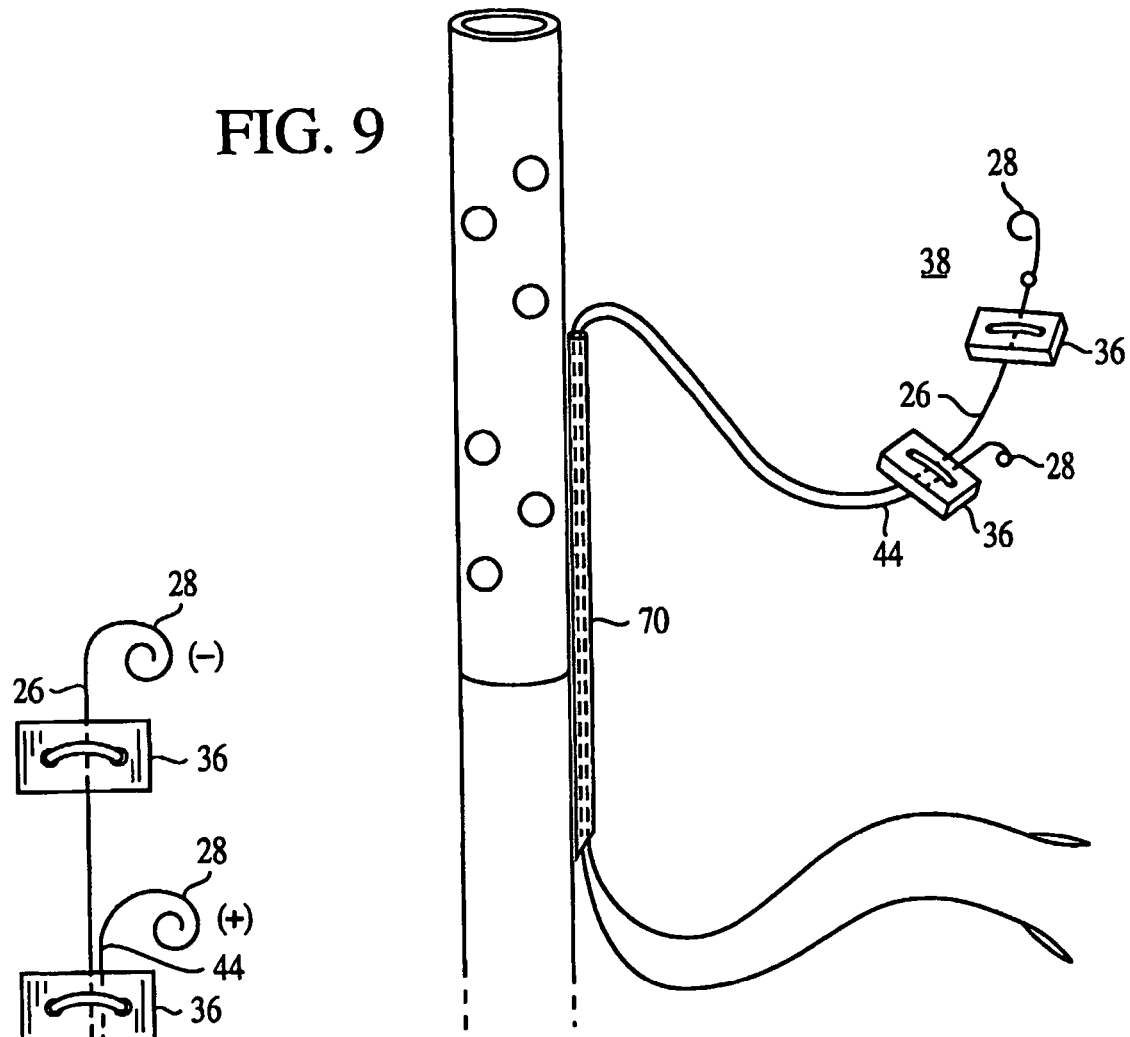
FIG. 9 shows schematically a bipolar heartwire in combination with a chest tube.
Figure 10:
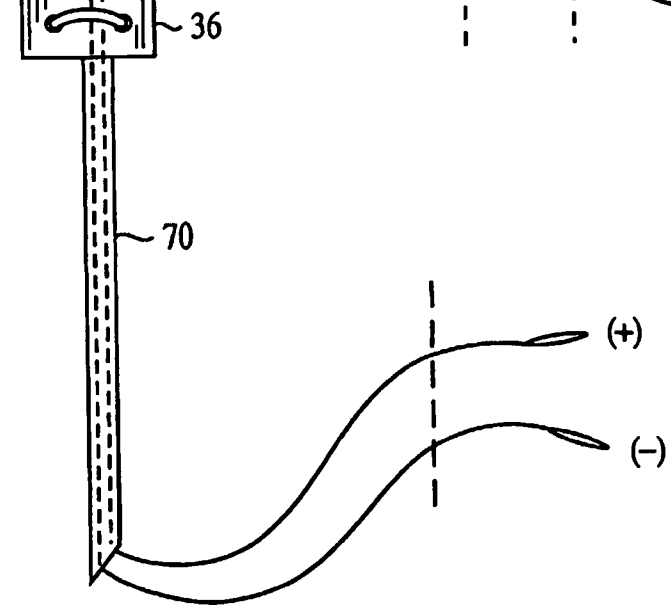
FIG. 10 is a more detailed view of a bipolar heartwire.

The foregoing embodiments have all included unipolar heartwires. As shown schematically in FIG. 9, bipolar heartwires are also usable with the various embodiments of the invention. A bipolar pacing wire is shown in more detail in FIG. 10. The two poles of the wire are closely adhered to each other as shown schematically at 70, and divide only at the distal end. The longer wire is the negative pole 26, with a coil 28, secured to the epicardium 38 by a pledget 36. The shorter wire, the positive pole 44, has its own coil 28 and pledget 36 which secure it to the epicardium for example about 1.5 cm from the negative pole 26.

Although the present invention has been described in relation to particular embodiments thereof, many other variations and modifications and other uses will become apparent to those skilled in the art. Therefore, the present invention is not limited by the specific disclosure herein.

What is claimed is:

1. In combination, a chest tube and a heartwire secured thereto;
    said heartwire comprising a wire having a proximal end and a distal end, at least part of the distal end being conductive so as to be usable in heart stimulation; and
    attached to said distal end, an end structure comprising an irregular or three-dimensional, atraumatic structure adapted for engaging a surgical material secured to the heart, for maintaining said heartwire in position relative to said surgical material and to said heart;
    wherein said heartwire is disposed in a groove formed in a peripheral wall of said chest tube;
    wherein said heartwire is removable from said groove while still maintaining said heartwire in position relative to said surgical material and to said heart; and
    wherein said groove is covered by a film which encloses said heartwire in said groove and is releasable for removing said heartwire from said groove.

2. The combination of claim 1, wherein atraumatic structure is a pledget.

3. The combination of claim 2, wherein said atraumatic structure further comprises a prolene suture.

4. The combination of claim 1, wherein said distal end of said heartwire is a pigtail.

5. The combination of claim 1, wherein said distal end of said heartwire is a tine.

6. The combination of claim 1, wherein said distal end of said heartwire is a coil.

7. The combination of claim 1, wherein said distal end of the heartwire is a hook.

8. The combination of claim 1, further comprising a second heartwire secured to said chest tube.

9. The combination of claim 8, wherein said second heartwire is disposed in a second groove formed in said peripheral wall of said chest tube.

10. The combination of claim 9, wherein said second heartwire is removable from said second groove while still maintaining said second heartwire in position relative to said surgical material and to said heart.

11. The combination of claim 10, wherein a distal end of said second heartwire is a pigtail.

* * * * *